United States Patent
Hoge et al.

(10) Patent No.: US 10,562,927 B2
(45) Date of Patent: Feb. 18, 2020

(54) BISMUTH PERFLUOROALKYLPHOSPHINATES AS LEWIS ACID CATALYSTS

(71) Applicant: MERCK PATENT GMBH, Darmstadt (DE)

(72) Inventors: Berthold Theo Hoge, Bielefeld (DE); Sven Joerg-Ruediger August Solyntjes, Bielefeld (DE); Nikolai (Mykola) Ignatiev, Duisburg (DE)

(73) Assignee: MERCK PATENT GMBH, Darmstadt (DE)

( * ) Notice: Subject to any disclaimer, the term of this patent is extended or adjusted under 35 U.S.C. 154(b) by 132 days.

(21) Appl. No.: 15/762,880

(22) PCT Filed: Sep. 7, 2016

(86) PCT No.: PCT/EP2016/001509
§ 371 (c)(1),
(2) Date: Mar. 23, 2018

(87) PCT Pub. No.: WO2017/050419
PCT Pub. Date: Mar. 30, 2017

(65) Prior Publication Data
US 2018/0273561 A1 Sep. 27, 2018

(30) Foreign Application Priority Data
Sep. 23, 2015 (DE) .................. 10 2015 012 194

(51) Int. Cl.
| | | |
|---|---|---|
| C07F 9/00 | (2006.01) | |
| C07F 9/94 | (2006.01) | |
| B01J 31/02 | (2006.01) | |
| C07B 37/02 | (2006.01) | |
| C07B 37/04 | (2006.01) | |
| C07B 41/06 | (2006.01) | |
| C07B 41/12 | (2006.01) | |
| C07B 43/08 | (2006.01) | |
| C07F 9/30 | (2006.01) | |
| C07B 37/12 | (2006.01) | |

(52) U.S. Cl.
CPC ............ *C07F 9/94* (2013.01); *B01J 31/0269* (2013.01); *C07B 37/02* (2013.01); *C07B 37/04* (2013.01); *C07B 41/06* (2013.01); *C07B 41/12* (2013.01); *C07B 43/08* (2013.01); *C07F 9/301* (2013.01); *C07B 37/12* (2013.01)

(58) Field of Classification Search
None
See application file for complete search history.

(56) References Cited

FOREIGN PATENT DOCUMENTS

DE 102013011081 A1 1/2015

OTHER PUBLICATIONS

International Search Report in PCT/EP2016/001509 dated Nov. 14, 2016.
Ramesh K. Metre et al: "Bismuth Phosphinates: Temperature-Dependent Formation of a Macrocycle and 1D Coordination Polymer", Phosphorus, Sulfur and Silicon and the Related Elements, vol. 190, No. 12, Oct. 19, 2015 (Oct. 19, 2015), US, pp. 2134-2141, XP055316414, ISSN: 1042-6507.
Magnus Rueping et al: "A review of new developments in the Friedel-Crafts alkylation—From green chemistry to asymmetric catalysis", Beilstein Journal of Organic Chemistry, vol. 6, Jan. 1, 2010 (Jan. 1, 2010), XP055316411.
Jorge Salvador et al: "Recent Advances of Bismuth(III) Salts in Organic Chemistry: Application to the Synthesis of Aliphatics, Alicyclics, Aromatics, Amino Acids and Peptides, Terpenes and Steroids of Pharmaceutical Interest", Mini-Reviews in Organic Chemistry, vol. 6, No. 4, Nov. 1, 2009 (Nov. 1, 2009), US, pp. 241-274, XP055316413, ISSN: 1570-193X.
"Acid Catalysis in Modem Organic Synthesis", Yamamoto et al. 2008, WILEY-VCH.
T. Ollevier, Org. Biomol. Chem., vol. 11, 2013, pp. 2740-2755.
F.H.A. Kwie et al., Synthetic Communications, vol. 40, 2010, pp. 1082-1087.
T.C. Wabnitz et al., Chem. Eur. J, vol. 10, 2004, pp. 484-493.
S. Kobayashi et al., Chem. Eur. J., vol. 12, 2006, pp. 5954-5960.
R. Qiu et al., Adv. Synth. Catal, vol. 352, 2010, pp. 153.
Nikolai V. Ignat'ev et al.: "Perfluoroalkylphosphorus acids: Synthesis, properties and applications in catalysis", Chimica OGGI/Chemistry Today, vol. 29, No. 5, Sep. 2011 (Sep. 1, 2011).
P. Pfeiffer et al., Ber. Dtsch. Chem. Ges., vol. 37, 1904, pp. 4620-4623.
Wasserscheid P; Keim W, Angew. Chem., vol. 112, 2000, pp. 3926.
S. K. De; R. A. Gibbs, Tetrahedron Letters, vol. 45, 2004, pp. 7407-7408.
N. M. Leonard; L. C. Wieland; R. S. Mohan, Tetrahedron, vol. 58, 2002, pp. 8373-8397.

*Primary Examiner* — Yun Qian
(74) *Attorney, Agent, or Firm* — Millen White Zelano & Branigan

(57) ABSTRACT

The invention relates to bismuth perfluoroalkylphosphinates as Lewis acid catalysts, the compounds, and processes for the preparation thereof.

$$Ar_xBi[OP(O)(R_f)_2]_{3-x} \qquad (Ia),$$

$$Ar_3Bi[OP(O)(R_f)_2]_2 \qquad (Ib).$$

8 Claims, No Drawings

BISMUTH PERFLUOROALKYLPHOSPHINATES AS LEWIS ACID CATALYSTS

The invention relates to bismuth perfluoroalkylphosphinates as Lewis acid catalysts, to the compounds, and to processes for the preparation thereof.

Catalysis using Lewis acids is a widespread method in organic synthesis and of outstanding importance for the industrial preparation of various substances. The numerous important industrial processes that are catalysed by Lewis acids include, for example, Friedel-Crafts alkylations and acylations of aromatic compounds, Gattermann-Koch reactions, Beckmann and Fries rearrangements, Mukaiyama aldol condensations [*Acid Catalysis in Modern Organic Synthesis*, H. Yamamoto and K. Ishihara (Eds.), WILEY-VCH, Weinheim, 2008].

G. N. Lewis defines an acid as a substance which is able to act as electron-pair acceptor. In accordance with this definition, Lewis acids are electron-deficient molecules or species. The Lewis-acidic catalysts usually used, such as $AlCl_3$, $TiCl_4$, $ZnCl_2$ and $BF_3$ diethyl etherate, are moisture-sensitive and generally cannot be recovered after completion of the reaction.

Further known Lewis acids are bismuth salts, such as $BiCl_3$, $BiBr_3$ and $Bi(OSO_2CF_3)_3$, as described in T. Ollevier, org. Biomol. Chem., 2013, 11, 2740-2755. When $BiCl_3$ is used as catalyst, however, a high concentration is necessary, generally 10 mol %, and the liberation of HCl can lead to corrosion of the reaction apparatus if, for example, steel vessels are used. The best-known bismuth catalyst is bismuth tris(trifluoromethanesulfonate). The disadvantage of this compound is the sensitivity to hydrolysis in the presence of water and its reactivity with alcohols and amines.

F. H. A. Kwie et al, Synthetic Communications, 40, 2010, 1082-1087 or T. C. Wabnitz et al, Chem. Eur. J. 10, 2004, 484-493, describe that any trifluoromethanesulfonic acid liberated from the bismuth tris(trifluoromethanesulfonate) could be responsible for the catalysis.

S. Kobayashi et al, Chem. Eur. J., 12, 2006, 5954-5960, propose that Bi(III) salts could be stabilised by the use of organic ligands, such as, for example, 2,2'-bipyridine derivatives.

R. Qiu et al, Adv. Synth. Catal, 352, 2010, 153 report on the use of bismuth perfluoroctanesulfonates as catalysts.

There therefore also continues to be a need for alternative Lewis acid catalysts in order that reactions catalysed by Lewis acids can be carried out optimally.

The object of the present invention is therefore to develop alternative Lewis acid catalysts which make it possible to carry out the desired catalysed reactions in good yield.

Surprisingly, it has been found that specific bismuth perfluoroalkylphosphinates are catalytically active and are significantly less sensitive to hydrolysis than bismuth tris (trifluoromethanesulfonate).

The invention therefore relates firstly to compounds of the formula (Ia) and (Ib)

$$Ar_xBi[OP(O)(R_f)_2]_{3-x} \quad (Ia),$$

$$Ar_3Bi[OP(O)(R_f)_2]_2 \quad (Ib)$$

where

Ar in each case, independently of one another, denotes an aryl group having 6 to 12 C atoms, which may be unsubstituted or substituted;

$R_f$ in each case, independently of one another, denotes a straight-chain or branched perfluoroalkyl group having 1 to 8 C atoms and x denotes 0, 1 or 2.

An aryl group having 6 to 12 C atoms denotes phenyl, naphthyl, anthracenyl or phenanthryl, which may be mono- or polysubstituted by halogen, alkyl, fluorinated alkyl, Oalkyl, $NO_2$ or CN.

"Alkyl" denotes a linear or branched alkyl group having 1 to 12 C atoms.

Halogen denotes F, Cl, Br or I. Halogen preferably denotes F or Cl.

"Fluorinated alkyl" is a linear or branched fluorinated alkyl group having 1 to 10 C atoms, where at least one H atom of a linear or branched alkyl group having 1 to 10 C atoms has been replaced by an F atom. It is also possible for all H atoms to have been replaced by F atoms.

The aryl group is preferably phenyl which is unsubstituted or monosubstituted by halogen, alkyl, fluorinated alkyl, Oalkyl $NO_2$ or CN. Ar is particularly preferably an unsubstituted phenyl group or a phenyl group which is monosubstituted by alkyl or by fluorinated alkyl. Ar is very particularly preferably an unsubstituted phenyl group.

A straight-chain or branched alkyl group having 1 to 12 C atoms is, for example, methyl, ethyl, isopropyl, propyl, butyl, sec-butyl or tert-butyl, pentyl, 1-, 2- or 3-methylbutyl, 1,1-, 1,2- or 2,2-dimethylpropyl, 1-ethylpropyl, n-hexyl, n-heptyl, n-octyl, n-nonyl, n-decyl, n-undecyl or n-dodecyl.

"Fluorinated alkyl" is preferably a straight-chain or branched fluorinated alkyl group having 1 to 4 C atoms. "Fluorinated alkyl" is particularly preferably trifluoromethyl, difluoromethyl, 2,2,2-trifluoroethyl, pentafluoroethyl, heptafluoroisopropyl, heptafluoropropyl and nonafluorobutyl.

In a preferred embodiment of the invention, the aryl group Ar is preferably identical on each occurrence.

The invention furthermore relates to compounds of the formula (Ia) and of the formula (Ib), as described above, where Ar is identical on each occurrence.

The perfluoroalkyl group $R_f$ is preferably trifluoromethyl, pentafluoroethyl, n-heptafluoropropyl, iso-heptafluoropropyl, n-nonafluorobutyl, sec-nonafluorobutyl or tert-nonafluorobutyl. The perfluoroalkyl group $R_f$ particularly preferably stands for pentafluoroethyl or n-nonafluorobutyl.

In a preferred embodiment of the invention, the perfluoroalkyl group $R_f$ is preferably identical on each occurrence.

The invention therefore furthermore relates to compounds of the formula (Ia) and (Ib), as described above or preferably described, in which the perfluoroalkyl group $R_f$ is identical on each occurrence.

Particularly preferred compounds of the formula (Ia) are the compounds phenylbis(pentafluoroethylphosphinyl)bismuth(III) and bismuth tris(pentafluoroethylphosphinate).

A particularly preferred compound of the formula (Ib) is triphenylbis[bis(pentafluoroethylphosphinyl)]bismuth(V).

The invention furthermore likewise relates to a process for the preparation of compounds of the formula (Ia), as described above or preferably described, in which x denotes 0, characterised in that bismuth is reacted with a compound of the formula (II)

$$HOP(O)(R_f)_2 \quad (II),$$

where $R_f$ in each case, independently of one another, denotes a straight-chain or branched perfluoroalkyl group having 1 to 8 C atoms.

Bismuth can be employed in any existing form of metal particles, for example in the form of powders or turnings. Bismuth is preferably employed as bismuth powder.

The compounds of the formula (II) are known perfluoroalkylphosphinic acids, some of which are commercially available or are accessible by known synthetic processes, as described, for example, in Nikolai V. Ignat'ev et al, Perfluoroalkylphosphorus acids: Synthesis, properties and applications in catalysis, Chimica Oggi/Chemistry Today, vol. 29, No. 5, September/October 2011.

The reaction can be carried out in the presence or absence of solvents.

Suitable solvents are, for example, methanol, ethanol, isopropanol, acetonitrile, propionitrile, benzonitrile, nitromethane, diethyl ether, methyl tert-butyl ether, 1,4-dioxane, 2-methyltetrahydrofuran, dichloromethane, 1,2-trichloroethane, monoglyme, diglyme, triglyme, chlorobenzene and ionic liquids or a mixture of the above-mentioned solvents.

Details on suitable ionic liquids are described below and also apply to this reaction. The reaction temperature is preferably between 20° C. and 180° C., particularly preferably between 60° C. and 160° C., very particularly preferably between 80° C. and 140° C.

This is preferably followed by a suitable purification method. For example, the reaction mixture is diluted with a suitable solvent, for example methanol, and the unreacted metal is filtered off. The filtrate is freed from the solvent, dried and, if necessary, purified further by washing, preferably with diethyl ether, and drying.

The invention furthermore relates to a process for the preparation of compounds of the formula (Ia), as described above or preferably described, in which x denotes 1 or 2, characterised in that a compound of the formula (II)

$$HOP(O)(R_f)_2 \qquad (II),$$

where $R_f$ in each case, independently of one another, denotes a straight-chain or branched perfluoroalkyl group having 1 to 8 C atoms, is reacted with triarylbismuthane, where the aryl in each case, independently of one another, denotes an aryl group having 6 to 12 C atoms.

The reaction, as described above, preferably takes place in an inert-gas atmosphere. It is particularly preferred if the oxygen content is a maximum of 1000 ppm.

The conditions with respect to the oxygen content do not apply to the work-up after successful reaction of the compounds of the formula (II), as described below.

Triarylbismuthanes are commercially available, for example triphenylbismuthane from ABCR, or can be prepared by known synthetic processes, as described in P. Pfeiffer et al, Ber. Dtsch. Chem. Ges. 1904, 37, 4620-4623. A preferred preparation is described in the example part. The definition of the aryl group and preferred aryl groups, as described above, apply correspondingly to these reactions. Triarylbismuthane can, for example, alternatively be prepared by reaction of aryllithium compounds, where aryl in each case, independently of one another, denotes an aryl group having 6 to 12 C atoms, with bismuth trichloride.

The reaction of the compounds of the formula (II) with triarylbismuthane is preferably carried out in the presence of a solvent.

Suitable solvents are, for example, alcohols, such as methanol or ethanol. The reaction temperature is preferably between 20° C. and 180° C., particularly preferably between 60° C. and 160° C., very particularly preferably between 80° C. and 140° C.

This is preferably followed by a suitable purification method. Preferably, all volatile constituents are removed in a high vacuum, and the residue is correspondingly washed and dried. The residue is preferably washed with water.

The invention furthermore relates to a process for the preparation of compounds of the formula (Ib), as described above or preferably described, characterised in that triarylbismuth(V) dichloride, in which aryl in each case, independently of one another, denotes an aryl group having 6 to 12 C atoms, which may be unsubstituted or substituted, is reacted with a compound of the formula (III), $$Ag[(R_f)_2PO_2] \qquad (III),$$

where $R_f$ in each case, independently of one another, denotes a straight-chain or branched perfluoroalkyl group having 1 to 8 C atoms.

The compounds of the formula (III) are silver salts of the corresponding bis(perfluoroalkyl)phosphinic acid and can be prepared by known processes. A reaction of silver oxide or silver carbonate with the bis(perfluoroalkyl)phosphinic acid is suitable. Further reaction conditions are known to the person skilled in the art and are described, for example, in the example part. The comments on suitable and preferred groups $R_f$ for compounds of the formula (Ia) also apply correspondingly to compounds of the formula (Ib).

Triarylbismuth(V) dichloride can be prepared, for example, by reaction of triarylbismuthane with chlorinating agents. Suitable chlorinating agents are $Cl_2$, $POCl_3$, $PCl_5$, $SOCl_2$ or $SO_2Cl_2$. $SO_2Cl_2$ is preferably employed. The reaction conditions can be derived by the person skilled in the art from similar reactions and are described, for example, in the example part.

The conversion to triarylbismuth(V) dichloride, as described above, is preferably carried out in an inert-gas atmosphere whose water content is a maximum of 1000 ppm.

The invention furthermore relates to a process for the preparation of compounds of the formula (Ib), as described above or preferably described, characterised in that a compound of the formula (II), $$HOP(O)(R_f)_2 \qquad (II),$$

where $R_f$ in each case, independently of one another, denotes a straight-chain or branched perfluoroalkyl group having 1 to 8 C atoms, is reacted with triarylbismuth(V) carbonate, triarylbismuth(V) diacetate or triarylbismuth(V) dichloride, where the aryl in each case, independently of one another, denotes an aryl group having 6 to 12 C atoms.

Some triarylbismuth(V) carbonates are commercially available, for example triphenylbismuth(V) carbonate from Sigma-Aldrich.

Some triarylbismuth(V) diacetates are commercially available, for example triphenylbismuth(V) diacetate from Sigma-Aldrich.

Suitable solvents are, for example, methanol, ethanol, isopropanol, acetonitrile, propionitrile, benzonitrile, nitromethane, diethyl ether, methyl tert-butyl ether, 1,4-dioxane, 2-methyltetrahydrofuran, dichloromethane, 1,2-dichloroethane, monoglyme, diglyme, triglyme, chlorobenzene and ionic liquids or a mixture of the above-mentioned solvents.

Details on suitable ionic liquids are described below and also apply to this reaction. The reaction temperature is preferably between 20° C. and 180° C., particularly preferably between 60° C. and 160° C., very particularly preferably between 80° C. and 140° C.

This is preferably followed by a suitable purification method. For example, the reaction mixture is diluted with a suitable solvent, for example methanol, and the unreacted metal is filtered off. The filtrate is freed from the solvent, dried and, if necessary, purified further by washing, preferably with diethyl ether, and drying.

The invention furthermore relates to the use of the compounds of the formula (Ia) and (Ib), as described above or described as preferred, as Lewis acid catalyst.

The invention furthermore relates to a Lewis acid catalyst of the formula (Ia) or (Ib), as described above or described as preferred, for use in a Lewis acid-catalysed reaction.

Very particularly preferred Lewis acid catalysts are the compounds phenyl-bis(pentafluoroethylphosphinyl)bismuth (III) and bismuth tris(pentafluoroethylphosphinate) as well as triphenylbis[bis(pentafluoroethylphosphinyl)]bismuth(V).

The compounds of the formula (Ia), of the formula (Ib) or the compounds of the formula (Ia) and (Ib) indicated as preferred are preferably employed in a catalyst amount of 0.01 to 20 mol %, based on the starting material in a sub-stoichiometric amount. The compounds of the formula (Ia) or (Ib), as described above or described as preferred, are particularly preferably employed in an amount of 0.1 mol % to 10 mol %. The compounds of the formula (Ia) or (Ib), as described above or described as preferred, are very particularly preferably employed in an amount of 1 mol % to 5 mol %. The person skilled in the art in the area of catalysis is able to select the optimum amount of catalyst for the corresponding reaction to be catalysed.

The comparative experiments with bismuth tris(trifluoromethanesulfonate) show that the compounds phenylbis(pentafluoroethylphosphinyl)bismuth(III) and bismuth tris(pentafluoroethylphosphinate) are not hygroscopic and can be stored in air. The compound triphenylbis[bis(pentafluoroethylphosphinyl)]bismuth(V) is likewise not hygroscopic.

In a preferred embodiment of the invention, the Lewis acid-catalysed reaction is selected from a condensation reaction, alcoholysis, aldol reaction, Mukaiyama aldol reaction, Gattermann-Koch reaction, Beckmann and Fries rearrangement, Friedel-Crafts acylation, Friedel-Crafts alkylation, Mannich reaction, Diels-Alder reaction, aza-Diels-Alder reaction, Baylis-Hillman reaction, Reformatsky reaction, Claisen rearrangement, Prins cyclisation reaction, allylation of carbonayl compounds, cyanation of aldehydes and ketones, cyanosilylation of aldehydes and ketones, Strecker reaction, 1,3-dipolar cycloaddition or Michael reaction.

The Lewis acid-catalysed reactions can be carried out in the presence or absence of corresponding solvents.

Suitable protic solvents on use of the Lewis acid catalysts according to the invention are ethanol, methanol or isopropanol.

Suitable aprotic solvents on use of the Lewis acid catalysts according to the invention are acetonitrile, propionitrile, benzonitrile, nitromethane, ethyl acetate, dimethylformamide, dimethylacetamide, dimethyl sulfoxide, N-methylpyrrolidone, diethyl ether, methyl tert-butyl ether 1,4-dioxane, tetrahydrofuran, 2-methyltetrahydrofuran, dichloromethane, 1,2-dichloroethane, monoglyme, diglyme, triglyme, hexane, heptane, petroleum ether, benzene and toluene.

The class of the ionic liquids are also suitable as solvents on use of the Lewis acid catalysts according to the invention.

An ionic liquid is taken to mean salts which generally consist of an organic cation and an inorganic anion. They do not contain any neutral molecules and usually have melting points below 373 K [Wasserscheid P, Keim W, 2000, *Angew. Chem.* 112, 3926]. Due to their salt character, ionic liquids have unique substance properties, such as, for example, a low vapour pressure, a liquid state over a broad temperature range, are non-flammable, exhibit high electrical conductivity and high electrochemical and thermal stability.

Suitable ionic liquids as solvents on use of the Lewis acid catalysts according to the invention are ionic liquids which have an organic cation and whose anion is selected from the group $Cl^-$, $Br^-$, $[R_1COO]^-$, $[R_1SO_3]^-$, $[R_2COO]^-$, $[R_2SO_3]^-$, $[R_1OSO_3]^-$, $[BF_4]^-$, $[SO_4]^{2-}$, $[HSO_4]^{1-}$, $[(R_1)_2P(O)O]^-$, $[R_1P(O)O_2]^{2-}$, $[(R_1O)_2P(O)O]^-$, $[(R_1O)P(O)O_2]^{2-}$, $[(R_2)_2P(O)O]^-$, $[R_2P(O)O_2]^{2-}$, $[(FSO_2)_2N]^-$, $[(R_2SO_2)_2N]^-$, $[(R_2SO_2)_3C]^-$, $[(FSO_2)_3C]^-$, $[P(R_2)_yF_{6-y}]^-$, $[BF_x(R_2)_{4-x}]^-$, $[BF_x(CN)_{4-x}]^-$, $[B(R_1)_a(CN)_{4-a}]^-$, $[B(R_2)F_2(CN)]^-$ or $[B(R_2)F(CN)_2]^-$, where $R_1$ in each case, independently of one another, denotes a linear or branched alkyl group having 1 to 12 C atoms, $R_2$ in each case, independently of one another, denotes a partially fluorinated or perfluorinated linear or branched alkyl group having 1 to 12 C atoms or pentafluorophenyl, x denotes the integer 0, 1, 2 or 3, y denotes the integer 0, 1, 2, 3 or 4 and a denotes the integer 1 or 2.

A perfluorinated linear or branched alkyl group having 1 to 4 C atoms is, for example, trifluoromethyl, pentafluoroethyl, n-heptafluoropropyl, iso-heptafluoropropyl, n-nonafluorobutyl, sec-nonafluorobutyl or tert-nonafluorobutyl. $R_2$ analogously defines a linear or branched perfluorinated alkyl group having 1 to 12 C atoms, including the above-mentioned perfluoroalkyl groups and, for example, perfluorinated n-hexyl, perfluorinated n-heptyl, perfluorinated n-octyl, perfluorinated ethylhexyl, perfluorinated n-nonyl, perfluorinated n-decyl, perfluorinated n-undecyl or perfluorinated n-dodecyl.

$R_2$ is preferably trifluoromethyl, pentafluoroethyl or nonafluorobutyl, very particularly preferably trifluoromethyl or pentafluoroethyl.

The variable y is preferably 1, 2 or 3, particularly preferably 3.

Preferred solvents are ionic liquids with the anions $[P(R_2)_yF_{6-y}]^-$ and $[R_2SO_3]^-$, where $R_2$ and y have a meaning indicated above or indicated as preferred.

Particularly preferred solvents are ionic liquids with the anions $[P(C_2F_5)_3F_3]^-$ and $[CF_3SO_3]^-$.

The organic cations are generally unrestricted and are preferably selected from imidazolium cations, pyridinium cations or pyrrolidinium cations, which may be appropriately substituted, as known from the prior art.

The ionic liquid 1-ethyl-3-methylimidazolium tris(pentafluoroethyl)trifluoro-phosphate {[EMIM][FAP]} and 1-ethyl-3-methylimidazolium triflate {[EMIM][OTf]} is very particularly preferably selected as solvent.

The following examples of Lewis acid-catalysed reactions show that the use of the compounds of the formula (Ia) and (Ib), as described above or described as preferred, the reactions can be carried out at reaction temperatures up to 120° C. and under air. The amount of catalyst is likewise significantly reduced in the case of the Lewis acid catalysts according to the invention.

The suitability of the compounds of the formula (Ia) and (Ib) as Lewis acid catalysts has been confirmed with reference to Friedel-Crafts acylations, a Friedel-Crafts alkylation, Diels-Alder reaction (addition) and Strecker reaction. These reaction types are representative of Lewis acid-catalysed reactions.

Even without further comments, it is assumed that a person skilled in the art will be able to utilise the following descriptions in the broadest scope. The preferred embodiments and examples should therefore merely be regarded as as descriptive disclosure which is absolutely not limiting in any way.

EXAMPLES

Example 1. Preparation of phenylbis(pentafluoroethylphosphinyl)-bismuth(III), PhBi[O(O)P($C_2F_5$)$_2$]$_2$

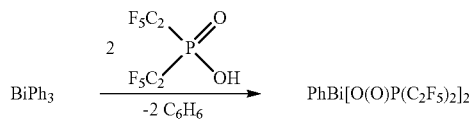

3.09 g (10.2 mmol) of bis(pentafluoroethyl)phosphinic acid, ($C_2F_5$)$_2$P(O)OH, in 15 ml of methanol are initially introduced in a 50 ml Schlenk flask in a counterstream of nitrogen, and 1.49 g (3.4 mmol) of triphenylbismuth are slowly added. The reaction mixture is heated under reflux for 24 hours. All volatile constituents of the reaction solution are removed in a high vacuum. The residue washed twice with water, and the residue obtained dried at 90° C. in a high vacuum, giving a colourless, finely powdered solid.

Yield of PhBi[O(O)P($C_2F_5$)$_2$]$_2$ (based on triphenylbismuth): 2.70 g (3.0 mmol, 89%). Decomposition point: >550° C.

IR: $\tilde{v}$=3074 (w), 1434 (w), 1309 (m), 1205 (vs), 1164 (s), 1135 (s), 1113 (s), 1070 (s), 999 (s), 963 (s), 750 (w), 728 (w), 689 (w), 634 (w), 599 (w), 569 (s), 498 (s), 442 (w), 428 (w).

TABLE

NMR data of phenylbis(pentafluoroethylphosphinyl)bismuth(III), PhBi[O(O)P($C_2F_5$)$_2$]$_2$ in acetone-$d_6$.

| Nucleus | δ [ppm] | Splitting | J [Hz] | Assignment |
|---|---|---|---|---|
| $^1$H | 9.2 | d | $^3J_{HH}$ = 7.0 | ortho H |
|  | 8.3 | t | $^3J_{HH}$ = 7.7 | meta H |
|  | 7.4 | t | $^3J_{HH}$ = 7.4 | para H |
| $^{13}$C-CPD | 138.2 |  |  | ortho C |
|  | 134.3 |  |  | meta C |
|  | 130.4 |  |  | para C |
| $^{13}$C, $^{19}$F- | 119.4 | d | $^3J_{CP}$ = 17.8 | $CF_3CF_2$ |
| DEPT135 | 112.1 | d | $^2J_{CP}$ = 140.6 | $CF_3CF_2$ |
| $^{19}$F | −81.2 | s | — | $CF_3CF_2$ |
|  | −125.5 | d | $^2J_{FP}$ = 77.0 | $CF_3CF_2$ |
| $^{31}$P | 0.6 | qui | $^2J_{FP}$ = 77.0 | P |

TABLE

Mass spectrometry data of phenylbis(pentafluoroethylphosphinyl)bismuth (III), PhBi[O(O)P($C_2F_5$)$_2$]$_2$, ESI negative.

| m/z | rel. intensity (%) | Fragment |
|---|---|---|
| 1188.6 | 100 |  |
| 964.7 | 90 |  |
| 904.6 | 30 |  |
| 602.6 | 40 |  |
| 300.7 | 40 | [P(O)O($C_2F_5$)$_2$]$^-$ |

Example 2. Preparation of Bi(III)[($C_2F_5$)$_2$PO$_2$]$_3$

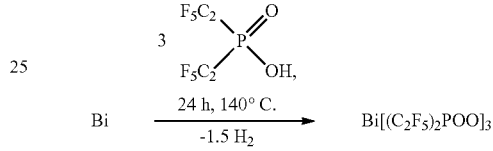

3.420 g (16.365 mmol) of ground bismuth powder are initially introduced in a 50 ml round-bottomed flask, and 15.544 g (51.469 mmol) of bis(pentafluoroethyl)-phosphinic acid are added via a pipette. The mixture is heated at 140° C. for 24 h. After cooling, the greyish reaction mixture is taken up in 25 ml of methanol, unreacted metal powder (Bi) is separated off by filtration, the filtrate is evaporated in a rotary evaporator and dried overnight in a high vacuum. The residue is taken up in 50 ml of diethyl ether, filtered and washed four times with 20 ml of diethyl ether each time. The colourless solid obtained is dried in a high vacuum. Yield (based on bismuth): 5.09 g (4.58 mmol, 28%).

Decomposition point: >490° C.

IR: $\tilde{v}$=1314 (w), 1213 (s), 1174 (m), 1160 (m), 1122 (s), 1083 (m), 1056 (m), 1003 (m), 958 (s), 752 (w), 641 (w), 601 (m), 571 (m), 519 (m), 496 (m), 473 (w), 429 (m).

TABLE

NMR data of Bi[($C_2F_5$)$_2$PO$_2$]$_3$ in methanol with acetone-$d_6$ as standard at RT.

| Nucleus | δ [ppm] | Splitting | J [Hz] | Assignment |
|---|---|---|---|---|
| $^{19}$F | −81.5 | s | — | $CF_3CF_2$ |
|  | −126.0 | d | $^2J_{FP}$ = 74.2 | $CF_3CF_2$ |
| $^{31}$P | 0.6 | qui | $^2J_{FP}$ = 74.2 | P |
| $^{13}$C, $^{19}$F- | 119.6 | d | $^2J_{CP}$ = 17.0 | $CF_3CF_2$ |
| DEPT135 | 112.4 | d | $^2J_{CP}$ = 138.2 | $CF_3CF_2$ |

No $^1$H signals are detected in the $^1$H-NMR spectrum for the solution Bi[($C_2F_5$)$_2$PO$_2$]$_3$ in acetone-$d_6$. This result confirms that Bi[($C_2F_5$)$_2$PO$_2$]$_3$ does not react with methanol at room temperature.

Example 3. Preparation of triphenylbis[bis(pentafluoroethyl)-phosphinyl)]bismuth(V), $Ph_3Bi[(C_2F_5)_2PO_2]_2$ A) Preparation of Silver(I) bis(pentafluoroethyl)phosphinate, $\{Ag[(C_2F_5)_2PO_2]\}$

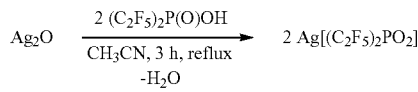

6.17 g of silver(I) oxide (26.63 mmol) are added in portions to a solution of $(C_2F_5)_2P(O)OH$ (15.03 g, 49.77 mmol) in acetonitrile (50 ml), and the reaction mixture is heated under reflux for 3 h. All insoluble components are filtered off, the solvent is removed under reduced pressure, and the residue is dried overnight in a high vacuum. The residue is taken up in diethyl ether (50 ml) and stirred over active carbon. After filtration and removal of the solvent, the colourless solid obtained is dried in a high vacuum.

The yield is 15.50 g (38.01 mmol, 76% based on $(C_2F_5)_2P(O)OH$).

$^{13}C\{^{19}F\}$ NMR ($CD_3CN$, RT), δ, ppm: 112.5 (d, $^1J(C,P)=127$ Hz; CF2), 119.5 (d, $^2J(C,P)=16$ Hz; CF3);

$^{19}F$ NMR ($CD_3CN$, RT), δ, ppm: −125.7 (d, $^2J(P,F)=69$ Hz, 4F; CF2), −81.1 (s, 6F; CF3);

$^{31}P$ NMR ($CD_3CN$, RT), δ, ppm: −0.2 (quint, $^2J(P,F)=69$ Hz).

B) Preparation of Triphenylbismuthane, $Ph_3Bi$ 5.52 g (795 mmol) of lithium in 250 ml of diethyl ether ($Et_2O$) are initially introduced in a 1 l three-necked flask with reflux condenser. 44 ml (420 mmol) of bromobenzene are slowly added dropwise via a 250 ml dropping funnel with stirring, so that the diethyl ether boils continuously. When the addition is complete, the grey-brown suspension is heated under reflux for 30 min, and 32.74 g (104 mmol) of bismuth trichloride are subsequently added. The mixture is stirred at RT for 15 h.

The suspension is hydrolysed using distilled water with ice-bath cooling and neutralised using a saturated ammonium chloride solution. The organic phase is separated off, and the aqueous phase is extracted twice with $Et_2O$. The combined organic phases are dried over $MgSO_4$, and the solvent is removed in a high vacuum. The residue is recrystallised from 80 ml of $Et_2O$. Repeated decantation and evaporation of the mother liquor and drying in a high vacuum gives triphenylbismuthane in the form of colourless needles.

The yield is 39.26 g (89.21 mmol, 86% based on bismuth trichloride).

$^1H$ NMR ($CDCl_3$), δ, ppm: 7.8 (m, Hortho), 7.4 (m, Hmeta, Hpara).

C) Conversion to triphenylbis[bis(pentafluoroethyl)phosphinyl)]bismuth(V), $Ph_3Bi[(C_2F_5)_2PO_2]_2$

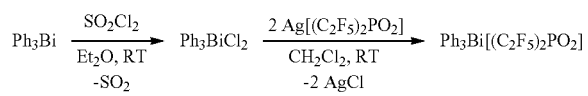

0.68 g (5.00 mmol) of $SO_2Cl_2$ are condensed onto a solution of triphenylbismuthane (1.58 g, 3.59 mmol) in dichloromethane (20 ml), and the reaction mixture is stirred at room temperature (RT) for one hour. All volatile constituents are removed in a high vacuum, until $Ph_3BiCl_2$ is obtained as a colourless solid. The residue is taken up in dichloromethane (20 ml), 3.24 g (7.20 mmol) of $Ag[(C_2F_5)_2PO_2]$ are added, and the reaction mixture is stirred at room temperature for one hour. The solid which precipitates out is filtered off, and the filtrate is evaporated under reduced pressure. The crude product is recrystallised from cyclohexane, and drying in a high vacuum gives $Ph_3Bi[(C_2F_5)_2PO_2]_2$ as colourless needles.

The yield is 2.61 g (2.50 mmol, 70% based on $BiPh_3$).

Melting point: 130-133° C., decomposition: >170° C.

$^1H$ NMR ($[D_6]$acetone, RT), δ, ppm: 7.7 (t, $^3J(H,H)=7$ Hz, 3H; Hpara), 7.9 (t, $^3J(H,H)=8$ Hz, 6H; Hmeta), 8.1 (d, $^3J(H,H)=8$ Hz, 6H; Hortho);

$^{13}C\{^1H\}$ NMR ($[D_6]$acetone, RT), δ, ppm: 133.0 (s; Cpara), 133.6 (s; Cmeta), 134.1 (s; Cortho), 155.2 (s, Cquart);

$^{13}C\{^{19}F\}$ NMR ($[D_6]$acetone, RT), δ, ppm: 110.9 (d, $^1J(C,P)=145$ Hz; $CF_2$), 118.1 (d, $^2J(C,P)=20$ Hz; $CF_3$);

$^{19}F$ NMR ($[D_6]$acetone, RT), δ, ppm: −124.3 (d, $^2J(P,F)=83$ Hz, 8F; $CF_2$), −80.7 (m, 12F; $CF_3$);

$^{31}P$ NMR ($[D_6]$acetone, RT), δ, ppm: 0.6 (quint, $^2J(P,F)=83$ Hz);

IR (solid): $\tilde{v}=408$ (w), 445 (s), 501 (s), 512 (s), 547 (w), 567 (s), 597 (m), 636 (w), 651 (w), 677 (m), 727 (m), 750 (w), 962 (s), 985 (s), 992 (s), 1047 (s), 1069 (m), 1105 (s), 1128 (s), 1147 (s), 1205 (vs), 1289 (s), 1442 (w), 1472 (w), 1561 (w), 3070 (vw) $cm^{-1}$;

MS (ESI): m/z (%): 741 (100) $[Ph_3Bi(C_2F_5)_2PO_2]^+$, 587 (10) $[PhBi(C_2F_5)_2PO_2]^+$, 363 (50) $[Ph_2Bi]^+$, 286 (90) $[BiPh]^+$, 209 (30) $[Bi]^+$; 301 (100) $[(C_2F_5)_2PO_2]^-$, 201 (20) $[(C_2F_5)PFO_2]^-$;

Elemental analysis calculated (found) [%] for $C_{26}H_{15}BiF_{20}O_4P_2$: C, 29.96 (C, 29.80); H, 1.45 (H, 1.53); (N, 0.13).

Comparative Example 4. Preparation of $Bi(OTf)_3$ (Anhydrous)

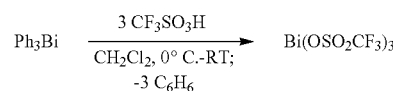

4.50 g (10.0 mmol) of triphenylbismuth in 100 ml of dried dichloromethane are initially introduced in a 250 ml Schlenk flask in a counterstream of nitrogen and cooled to −70° C. in a cooling bath. 2.7 ml (31.0 mmol) of trifluoromethanesulfonic acid (triflic acid) are then added slowly, and the reaction mixture is warmed to room temperature overnight. The reaction mixture is filtered under an inert atmosphere. The residue obtained is washed twice with dichloromethane and dried in a high vacuum, giving 5.59 g (8.5 mmol) of a beige solid. The yield of $Bi(OTf)_3$ is 85%.

The NMR analytical data correspond to the values indicated in the literature [M. Labrouillere, et al., *Tetrahedron Lett.*, 40 (1999), p. 285-286].

Examples for the Determination of the Catalytic Activity:

The catalysis reactions selected are carried out in 10-25 ml Schlenk tubes and under standard Schlenk conditions. Firstly, the bismuth perfluoroalkylphosphinate is weighed in and the corresponding stoichiometry of the starting materials and of the solvent is adjusted.

In order to calculate the conversion, a component having previously selected, characteristic NMR signals is employed in a sub-stoichiometric amount. If these marker signals are no longer detected in the NMR signal spectrum, quantitative conversion can be assumed. No further work-up or determination of isolated yields is carried out. The times are taken after addition of the starting material employed in sub-stoichiometric amount. The end point is sampling.

Blank samples were carried out for confirmation of the catalytic activity.

Comparative Example 5. Friedel-Crafts Acylation with $Bi(OSO_2CF_3)_3$ as Catalyst

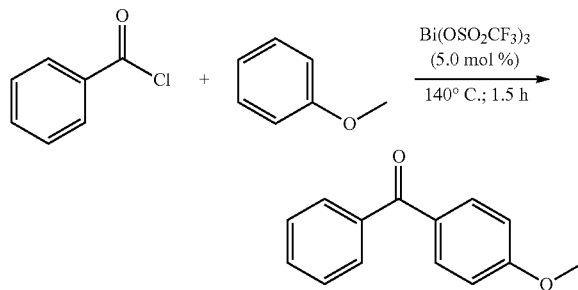

225 mg (0.343 mmol) of $Bi(OTf)_3$ and 1.051 g (7.48 mmol) of benzoyl chloride are initially introduced in a 25 ml Schlenk tube in a counterstream of nitrogen. 735 mg (6.80 mmol) of anisole are added, and the mixture is stirred at 140° C. for 1.5 hours. The reaction mixture rapidly becomes yellow, later becomes a dark red colour and is solid at room temperature.

According to $^1$H- and $^{13}$C-NMR spectroscopy investigations, the conversion to 4-methoxybenzophenone is 80%.

Example 6. Friedel-Crafts Acylation with $Bi[(C_2F_5)_2 PO_2]_3$ as Catalyst

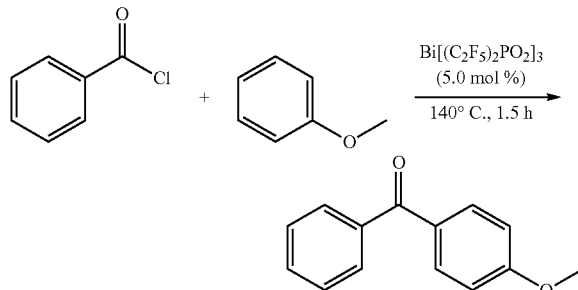

149 mg (0.134 mmol) of $Bi[(C_2F_5)_2PO_2]_3$ and 441 mg (3.137 mmol) of benzoyl chloride are initially introduced in a 25 ml Schlenk tube in a counterstream of nitrogen. 293 mg (2.710 mmol) of anisole are added, and the mixture is stirred at 140° C. for 1.5 hours. The solution rapidly becomes yellow, later dark red.

The conversion to 4-methoxybenzophenone detected by $^1$H- and $^{13}$C-NMR spectroscopy is 90%.

The reaction product is obtained by extraction of the reaction mixture with diethyl ether. The extract is washed twice with water and concentrated $NaHCO_3$ solution. The organic phase is dried over magnesium sulfate, and the solvent is distilled off under reduced pressure. The residue is crystallised from n-hexane/diethyl ether (2:1).

Example 7. Friedel-Crafts Acylation with PhBi $[(C_2F_5)_2P(O)O]_2$ as Catalyst

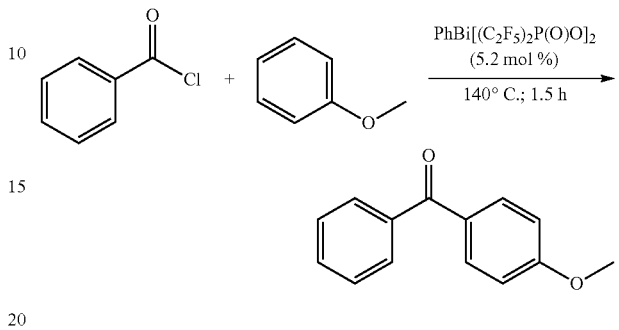

119 mg (0.134 mmol) of PhBi(III) bis(perfluoroalkylphosphinate) and 850 mg (6.05 mmol) of benzoyl chloride are initially introduced in a 25 ml Schlenk tube in a counterstream of nitrogen. 280 mg (2.59 mmol) of anisole are added, and the mixture is stirred at 140° C. for 1.5 hours. The solution rapidly becomes yellow, later dark red.

According to $^1$H- and $^{13}$C-NMR spectroscopy investigations, the conversion to 4-methoxybenzophenone is 81%.

Comparative Example 8. Friedel-Crafts Acylation with $(C_2F_5)_2P(O)OH$ as Catalyst

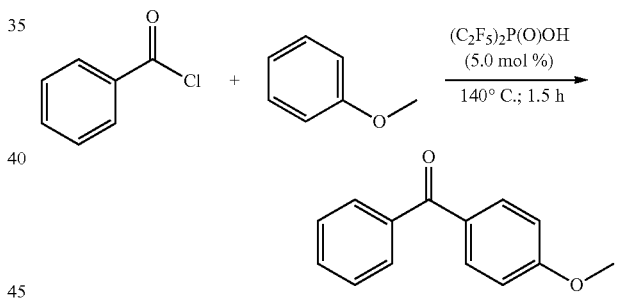

85 mg (0.281 mmol) of bis(pentafluoroethyl)phosphinic acid, $(C_2F_5)_2P(O)OH$, and 880 mg (6.26 mmol) of benzoyl chloride are initially introduced in a 25 ml Schlenk tube in a counterstream of nitrogen. 610 mg (5.64 mmol) of anisole are added, and the mixture is stirred at 140° C. for 1.5 hours. The solution becomes dark red after a short time.

According to $^1$H- and $^{13}$C-NMR spectroscopy investigations, the conversion to 4-methoxybenzophenone is 29%.

Example 9. Investigations of the Hygroscopy of $Bi(OTf)_3$, $Bi[(C_2F_5)_2P(O)O]_3$ and $PhBi[(C_2F_5)_2P(O)O]_2$ on Storage in Air a) Finally powdered, ochre-coloured bismuth tris(trifluoromethanesulfonate), $Bi(OTf)_3$, (anhydrous; 278 mg; 0.40 mmol) is stored on a watch glass in ambient air. After 24 hours, an increase in weight of 67 mg is observed. This corresponds to the weight of nine equivalents of $H_2O$ (3.6 mmol). The product changes visually.

b) In a comparable experiment, 181 mg (0.20 mmol) of finely powdered, colourless PhBi bis(pentafluoroethylphosphinate), PhBi[(C₂F₅)₂P(O)O]₂ (anhydrous) are stored on a watch glass in ambient air. After 24 hours, an increase in weight of 1 mg is observed. The product does not change visually.

c) Bi[(C₂F₅)₂PO₂]₃: 188 mg (0.169 mmol) of finely powdered, colourless Bi[(C₂F₅)₂PO₂]₃ (anhydrous) are stored on a watch glass in ambient air. After 24 h, an increase in weight of 2 mg is detected. The product does not change visually.

These experiments show that Bi[(C₂F₅)₂P(O)O]₃ and PhBi[(C₂F₅)₂P(O)O]₂ are virtually non-hygroscopic compared with bismuth triflate, Bi(OTf)₃.

Comparative Example 10. Friedel-Crafts Acylation with Bi(OSO₂CF₃)₂·nH₂O (Stored in Air for 24 Hours) as Catalyst

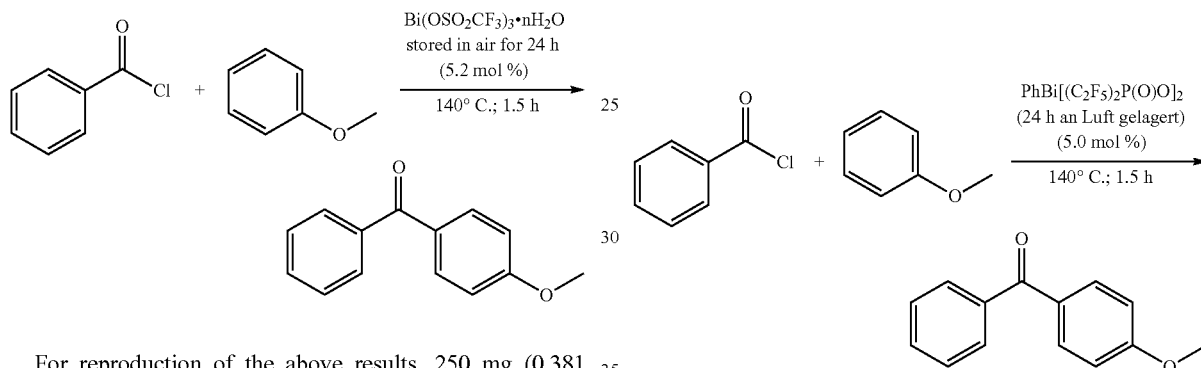

For reproduction of the above results, 250 mg (0.381 mmol) of finely powdered, ochre-coloured Bi(OTf)₃ (anhydrous) are stored on a watch glass in ambient air. After 24 h, an increase in weight of 66 mg is detected. This corresponds to the weight of 9.6 equivalents of H₂O (3.442 mmol). The crumbly and clay-coloured solid is transferred into a 25 ml Schlenk tube and employed as catalyst in a Friedel-Crafts acylation. 1.298° mg (9.271 mmol) of benzoyl chloride and 806 mg (7.459 mmol) of anisole are added under ambient air, and the mixture is stirred at 140° C. for 1.5 h. The reaction mixture becomes a dark red colour and is solid at RT. The conversion to 4-methoxybenzophenone detected by ¹H- and ¹³C-NMR spectroscopy is 72%.

Example 11. Friedel-Crafts Acylation with Bi[(C₂F₅)₂PO₂]₃ (Stored in Air for 24 Hours) as Catalyst Bi[(C₂F₅)₂PO₂]₃: 188 mg (0.169 mmol) of finely powdered, colourless Bi[(C₂F₅)₂PO₂]₃ (anhydrous) are stored on a watch glass in ambient air. After 24 h, an increase in weight of 2 mg is detected. The colourless, finely powdered solid obtained is transferred into a 25 ml Schlenk tube and employed as catalyst in a Friedel-Crafts acylation.

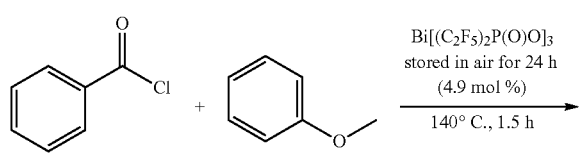

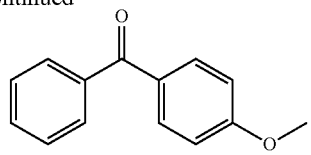

571 mg (64.062 mmol) of benzoyl chloride and 372 mg (3.440 mmol) of anisole are added under ambient air, and the mixture is stirred at 140° C. for 1.5 h. The reaction mixture rapidly becomes a yellow colour and later deep red. The conversion to 4-methoxybenzophenone detected by ¹H- and ¹³C-NMR spectroscopy is 85%, with the advantage that a smaller amount of catalyst can be employed than in Comparative Example 9.

Example 12. Friedel-Crafts Acylation with PhBi[(C₂F₅)₂P(O)O]₂ (Stored in Air for 24 Hours) as Catalyst

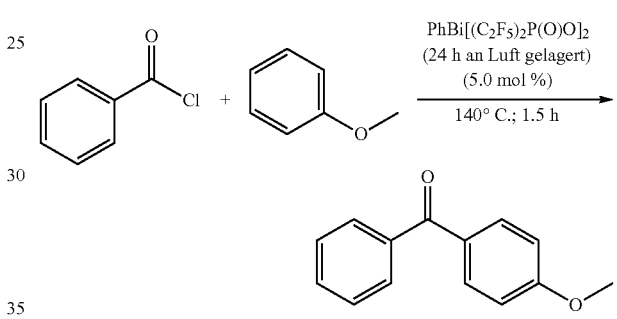

268 mg (0.302 mmol) of finely powdered, colourless PhBi bis(pentafluoroethylphosphinate), PhBi[(C₂F₅)₂P(O)O]₂, (anhydrous) are stored on a watch glass in ambient air. After 24 hours, an increase in weight of 3 mg is observed. The colourless, finely powdered solid obtained is employed in a Friedel-Crafts acylation. 924 mg (6.57 mmol) of benzoyl chloride and 648 mg (5.99 mmol) of anisole are added under ambient air, and the mixture is stirred at 140° C. for 1.5 hours. The reaction mixture rapidly becomes a yellow colour and later deep red. According to ¹H- and ¹³C-NMR spectroscopy investigations, conversion to 4-methoxybenzophenone is 83%.

TABLE

Overview of the Friedel-Crafts acylations of anisole and benzoyl chloride carried out with various catalyst systems.

| Catalyst[a] | Conversion[b] |
|---|---|
| Bi(OTf)₃ (anhydrous) | 80% |
| Bi(OTf)₃ * n H₂O (stored in air for 24 h) | 72% |
| (C₂F₅)₂P(O)OH | 29% |
| PhBi[(C₂F₅)₂P(O)O]₂ | 81% |
| PhBi[(C₂F₅)₂P(O)O]₂ (stored in air for 24 h) | 83% |
| Bi[(C₂F₅)₂P(O)O]₃ | 90% |
| Bi[(C₂F₅)₂P(O)O]₃ (stored in air for 24 h) | 85% |

[a] Amount of catalyst: about 5 mol %; reaction conditions: 1.5 h, 140° C.;
[b] Conversion calculations are based on ¹H- and ¹³C-NMR spectroscopy measurements based on anisole.

Example 13. Friedel-Crafts Alkylation with PhBi[(C₂F₅)₂P(O)O]₂ as Catalyst

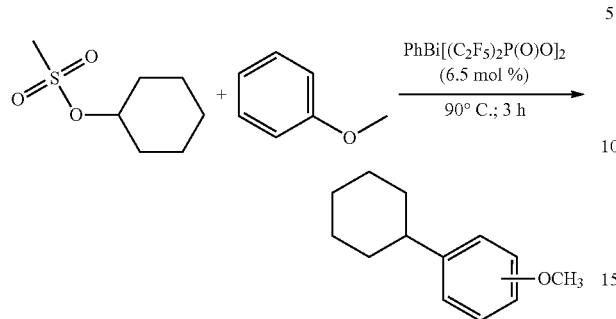

335 mg (0.377 mmol) of Bi(III) phosphinate complex, PhBi[(C₂F₅)₂P(O)O]₂, and 1.036 g (5.812 mmol) of cyclohexylmethanesulfonate are initially introduced in a 25 ml Schlenk tube in a counterstream of nitrogen. 1.295 g (11.974 mmol) of anisole are added, and the mixture is stirred at 90° C. After 3 h, quantitative conversion is detected via ¹H- and ¹³C-NMR spectroscopy investigations. The NMR analysis data correspond to the values known from the literature [R. P. Singh, R. M. Kamble, K. L. Chandra, P. Saravanan, V. K. Singh, *Tetrahedron,* 2001, 57, 241-247; H. Kotsuki, T. Oshisi, M. Inoue, *Synlett,* 1998, 1998, 255-256].

Example 14. Diels-Alder Addition with PhBi[(C₂F₅)₂P(O)O]₂ as Catalyst

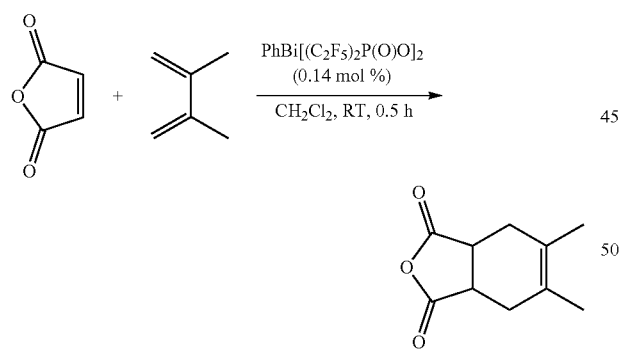

13 mg (0.0146 mmol) of Bi(III) phosphinate complex, PhBi[(C₂F₅)₂P(O)O]₂, and 993 mg (10.127 mmol) of maleic anhydride are suspended in 5 ml of dichloromethane in a 25 ml Schlenk tube in a counterstream of nitrogen. 2.45 g (3.37 ml, 29.83 mmol) of 2,3-dimethylbutadiene are added, and the mixture is stirred at room temperature. After 30 min, quantitative conversion is detected via ¹H- and ¹³C-NMR spectroscopy investigations.

The NMR analysis data correspond to the values known from the literature [C. E. Song, E. J. Roh, S.-g. Lee, W. H. Shim, J. H. Choi, *Chem. Commun.* 2001, p. 1122-1123].

Example 15. Diels-Alder Addition with PhBi[(C₂F₅)₂P(O)O]₂ as Catalyst

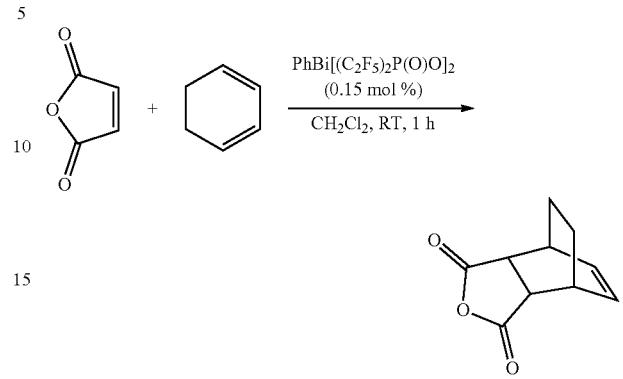

12 mg (0.0135 mmol) of Bi(III) phosphinate complex, PhBi[(C₂F₅)₂P(O)O]₂, and 893 mg (9.107 mmol) of maleic anhydride are suspended in 5 ml of dichloromethane in a 25 ml Schlenk tube in a counterstream of nitrogen. 2.20 g (2.6 ml, 27.48 mmol) of 1,3-cyclohexadiene are added, and the mixture is stirred at room temperature. The solution immediately becomes a yellow colour. After 1 h, quantitative conversion is detected via ¹H- and ¹³C-NMR spectroscopy investigations.

The NMR analysis data correspond to the values known from the literature [C. E. Song, E. J. Roh, S.-g. Lee, W. H. Shim, J. H. Choi, *Chem. Commun.* 2001, p. 1122-1123].

Example 16. Strecker Reaction Catalysed by PhBi[(C₂F₅)₂P(O)O]₂

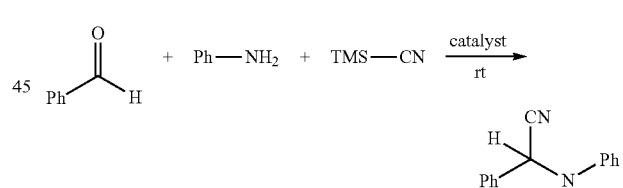

117 mg (0.132 mmol) of Bi(III) phosphinate complex, PhBi[(C₂F₅)₂P(O)O]₂, are suspended in 5 ml of dichloromethane in a 25 ml Schlenk tube, and 0.20 ml (210 mg; 1.978 mmol) of benzaldehyde and 0.18 ml (184 mg; 1.972 mmol) of aniline are added, and the mixture is stirred at room temperature. In order to initiate the reaction, 0.37 ml (292 mg; 2.946 mmol) of trimethylsilyl cyanide are added. After 30 min, quantitative conversion is detected via ¹H- and ¹³C-NMR spectroscopy investigations. The NMR analysis data correspond to the values known from the literature.

The results are summarised in the following table in comparison with data known from the literature.

TABLE

Comparison of the reaction conditions, amounts of catalyst and conversions of the Strecker reaction of benzaldehyde and aniline of catalysts known from the literature and of the Bi(III) phosphinate complex.

| Catalyst | [mol %] | Solvent | Time | Conversion |
|---|---|---|---|---|
| [1] $BiCl_3$ | 10 | $CH_3CN$ | 10 h | 84% |
| [2] $Bi(NO_3)_3$ | 10 | $CH_3CN$ | 1 h | 94% |
| $PhBi[(C_2F_5)_2P(O)O]_2$ | 6.7 | $CH_2Cl_2$ | 0.5 h | >97%* |

*Conversion calculations are based on $^1$H- and $^{13}$C-NMR spectroscopy measurements based on benzaldehyde.

[6] S. K. De, R. A. Gibbs, *Tetrahedron Letters*, 2004, 45, 7407-7408.

[7] N. M. Leonard, L. C. Wieland, R. S. Mohan, *Tetrahedron*, 2002, 58, 8373-8397.

Example 17. Strecker Reaction Catalysed by PhBi[(C$_2$F$_5$)$_2$P(O)O]$_2$

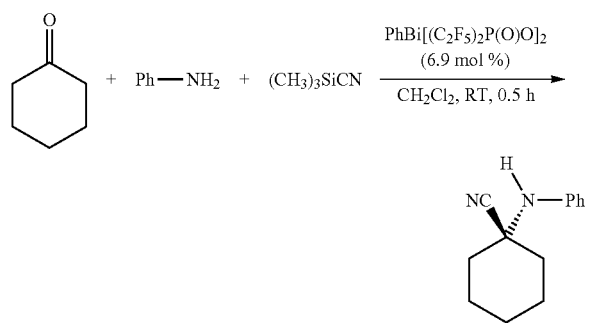

107 mg (0.121 mmol) of Bi(III) phosphinate complex, $PhBi[(C_2F_5)_2P(O)O]_2$, are suspended in 5 ml of dichloromethane in a 25 ml Schlenk tube in a counterstream of nitrogen and 0.18 ml (0.171 mg; 1.742 mmol) of cyclohexanone and 0.18 ml (0.184 mg; 1.972 mmol) of aniline are added, and the mixture is stirred at room temperature. In order to initiate the reaction, 0.32 ml (253 mg; 2.548 mmol) of trimethylsilyl cyanide are added. After 30 min, quantitative conversion is detected via $^1$H- and $^{13}$C-NMR spectroscopy investigations. The NMR analysis data correspond to the values known from the literature [G. K. S. Prakash, T. Mathew, C. Panja, S. Alconcel, H. Vaghoo, C. Do, G. A. Olah, *Proceedings of the National Academy of Sciences*, 2007, 104, 3703-3706].

Example 18. Diels-Alder Addition with Ph$_3$Bi[(C$_2$F$_5$)$_2$PO$_2$]$_2$ as Catalyst

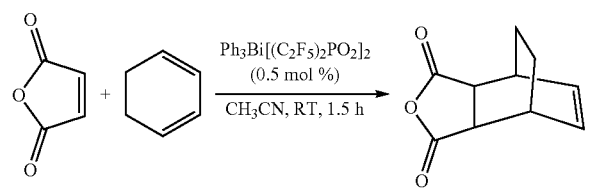

28 mg (0.027 mmol) of $Ph_3Bi[(C_2F_5)_2PO_2]_2$ and 624 mg (6.364 mmol) of maleic anhydride are dissolved in 4 ml of acetonitrile in a 25 ml Schlenk tube in a counterstream of nitrogen. 862 mg (1.0 ml, 10.753 mmol) of 1,3-cyclohexadiene are added, and the mixture is stirred at room temperature. The solution immediately becomes a yellow colour and becomes cloudy. After 1.5 h, quantitative conversion is detected via $^1$H- and $^{13}$C-NMR spectroscopy investigations. The NMR analysis data correspond to the values known from the literature [C. E. Song, E. J. Roh, S.-G. Lee, W. H. Shim, J. H. Choi, *Chem. Commun.* 2001, p. 1122-1123].

Example 19. Friedel-Crafts Acylation with Ph$_3$Bi[(C$_2$F$_5$)$_2$PO$_2$]$_2$ as Catalyst

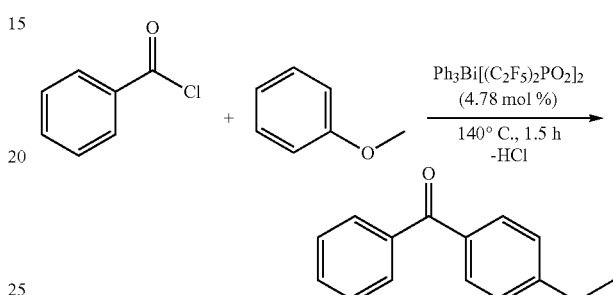

59 mg (0.057 mmol) of $Ph_3Bi[(C_2F_5)_2PO_2]_2$ and 299 mg (2.127 mmol) of benzoyl chloride are initially introduced in a 25 ml Schlenk tube in a counterstream of nitrogen. 128 mg (1.184 mmol) of anisole are added, and the mixture is stirred at 140° C. for 1.5 hours. The solution rapidly becomes yellow, later dark red. The conversion to 4-methoxybenzophenone detected by $^1$H- and $^{13}$C-NMR spectroscopy is 86%.

Example 20. Friedel-Crafts Acylation with Ph$_3$Bi[(C$_2$F$_5$)$_2$PO$_2$]$_2$ (Stored in Air for 24 Hours) as Catalyst

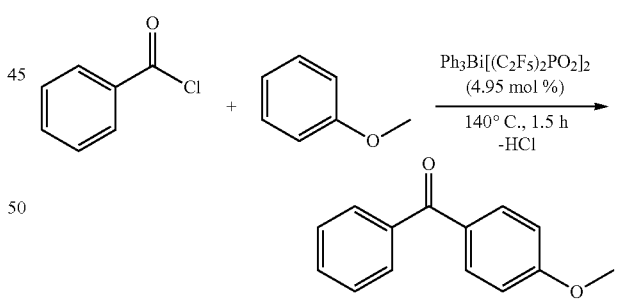

In order to investigate the hygroscopy behaviour, 145 mg (0.139 mmol) of colourless, needle-shaped $Ph_3Bi[(C_2F_5)_2PO_2]_2$ are stored on a watch glass in ambient air. After 24 h, no increase in weight is detected. The colourless, needle-shaped solid obtained is transferred into a 25 ml Schlenk tube and employed as catalyst in a Friedel-Crafts acylation. 614 mg (4.368 mmol) of benzoyl chloride and 304 mg (2.811 mmol) of anisole are added under ambient air, and the mixture is stirred at 140° C. for 1.5 h. The solution rapidly becomes yellow, later dark red. The conversion to 4-methoxybenzophenone detected by $^1$H- and $^{13}$C-NMR spectroscopy is 88%.

Example 21. Preparation of Ph₂Bi[O(O)P(C₂F₅)₂]

0.82 g (2.7 mmol) of bis(pentafluoroethyl)phosphinic acid are added dropwise to a solution of 1.25 g (2.84 mmol) of tiphenylbismuth in dichloromethane (30 ml). The reaction mixture is heated under reflux for 5 hours. The supernatant solution is decanted, and the solid which remains is washed twice with dichloromethane (10 ml) and dried in a high vacuum, giving a colourless, finely powdered solid. Yield of Ph₂Bi[O(O)P(C₂F₅)₂]: 1.41 g (2.1 mmol, 78%). Melting point: 270° C.

TABLE

NMR data of Ph₂Bi[O(O)P(C₂F₅)₂] in [D₄]methanol, RT

| Nucleus | δ [ppm] | Splitting | J [Hz] | Assignment |
|---|---|---|---|---|
| $^1$H | 8.4 | m | | ortho H |
| | 7.9 | m | | meta H |
| | 7.5 | m | | para H |
| $^{13}$C{$^1$H} | 194.3 | s | | C$_{quart}$ |
| | 136.8 | s | | C$_{ortho}$ |
| | 132.1 | s | | C$_{meta}$ |
| | 129.1 | s | | C$_{para}$ |
| $^{13}$C{$^{19}$F} | 119.0 | d | $^2J_{CP}$ = 17.0 | CF$_3$CF$_2$ |
| | 111.8 | d | $^1J_{CP}$ = 137.0 | CF$_3$CF$_2$ |
| $^{19}$F | −82.0 | m | — | CF$_3$CF$_2$ |
| | −126.7 | d | $^2J_{PF}$ = 74.0 | CF$_3$CF$_2$ |
| $^{31}$P | −0.2 | qui | $^2J_{FP}$ = 74.0 | P |

Example 22: Preparation of PhBi[O(O)P(C₄F₉)₂]₂

An aqueous solution of bis(nonafluorobutyl)phosphinic acid is evaporated to dryness over the course 24 hours, giving 7.63 g (15.2 mmol) of the acid as a solid. This acid is added to a solution of 2.20 g (5 mmol) of triphenylbismuth in methanol (50 ml), and the reaction mixture is heated under reflux for 20 hours. Insoluble components are filtered, and the solvent is removed under reduced pressure. After addition of diethyl ether (50 ml), the solid which has precipitated out is filtered, washed four times with diethyl ether (20 ml) and dried in a high vacuum.

Yield of PhBi[O(O)P(C₄F₉)₂]₂: 4.35 g (3.4 mmol, 68%). Decomposition point: >490° C.

TABLE

NMR data of PhBi[O(O)P(C₄F₉)₂]₂ in [D₄]methanol, RT

| Nucleus | δ [ppm] | Splitting | J [Hz] | Assignment |
|---|---|---|---|---|
| $^1$H | 8.8 | m | | ortho H |
| | 8.3 | m | | meta H |
| | 7.6 | m | | para H |
| $^{13}$C{$^1$H} | 230.9 | s | | C$_{quart}$ |
| | 137.1 | s | | C$_{ortho}$ |
| | 134.2 | s | | C$_{meta}$ |
| | 129.9 | s | | C$_{para}$ |
| $^{13}$C{$^{19}$F} | 109.0 | d | $^3J_{CP}$ = 3 | CF$_3$CF$_2$CF$_2$CF$_2$ |
| | 111.3 | d | $^2J_{CP}$ = 10 | CF$_3$CF$_2$CF$_2$CF$_2$ |
| | 114.5 | d | $^1J_{CP}$ = 134 | CF$_3$CF$_2$CF$_2$CF$_2$ |
| | 117.5 | s | | CF$_3$ |
| $^{19}$F | −82.6 | m | — | CF$_3$ |
| | −121.9 | m | | CF$_3$CF$_2$CF$_2$CF$_2$ |
| | −122.9 | dm | $^2J_{PF}$ = 75 | CF$_3$CF$_2$CF$_2$CF$_2$ |
| | −127.1 | m | | CF$_3$CF$_2$CF$_2$CF$_2$ |
| $^{31}$P | 1.1 | qui | $^2J_{PF}$ = 75 | P |

The invention claimed is:

1. A compound of formula (Ia) or (Ib)

$$Ar_xBi[OP(O)(R_f)_2]_{3-x} \quad \text{(Ia)},$$

$$Ar_3Bi[OP(O)(R_f)_2]_2 \quad \text{(Ib)}$$

where
Ar in each case, independently of one another, denotes an aryl group having 6 to 12 C atoms, which is unsubstituted or optionally substituted;
$R_f$ in each case, independently of one another, denotes a straight-chain or branched perfluoroalkyl group having 1 to 8 C atoms and
x denotes 0, 1 or 2.

2. The compound according to claim 1, where Ar is identical on each occurrence.

3. The compound according to claim 1, where the perfluoroalkyl group $R_f$ is identical on each occurrence.

4. The compound according to claim 1, where $R_f$ is selected from pentafluoroethyl or n-nonafluorobutyl.

5. A process for the preparation of compounds of the formula (Ia) according to claim 1, where x denotes 1 or 2, comprising:
reacted a compound of the formula (II)

$$HOP(O)(R_f)_2 \quad \text{(II)},$$

where
$R_f$ in each case, independently of one another, denotes a straight-chain or branched perfluoroalkyl group having 1 to 8 C atoms.

6. A process for the preparation of compounds of the formula (Ib) according to claim 1, comprising:
converting triarylbismuthane to triaryldichlorobismuthane, where aryl in each case, independently of one another, denotes an aryl group having 6 to 12 C atoms, which is unsubstituted or optionally substituted, and
reacting triaryldichlorobismuthane with a compound of the formula (III), $$Ag[(R_f)_2PO_2] \quad \text{(III)},$$

where
$R_f$ in each case, independently of one another, denotes a straight-chain or branched perfluoroalkyl group having 1 to 8 C atoms.

7. A process for the preparation of compounds of the formula (Ib) according to claim 1, comprising reacting a compound of the formula (II), $$HOP(O)(R_f)_2 \quad \text{(II)},$$

where
$R_f$ in each case, independently of one another, denotes a straight-chain or branched perfluoroalkyl group having 1 to 8 C atoms,
with
triarylbismuth(V) carbonate, triarylbismuth(V) diacetate or triarylbismuth(V) dichloride, where the aryl in each case, independently of one another, denotes an aryl group having 6 to 12 C atoms.

8. A Lewis acid catalyst, comprising a compound according to claim 1.

* * * * *

UNITED STATES PATENT AND TRADEMARK OFFICE
CERTIFICATE OF CORRECTION

PATENT NO. : 10,562,927 B2  
APPLICATION NO. : 15/762880  
DATED : February 18, 2020  
INVENTOR(S) : Berthold Theo Hoge Page 1 of 1

It is certified that error appears in the above-identified patent and that said Letters Patent is hereby corrected as shown below:

In the Claims

Column 20, Line 24, Claim 5, change "reacted" to -- reacting --;

Column 20, Line 31, Claim 5, after "atoms" insert -- , with triarylbismuthane, where the aryl in each case, independently of one another, denotes an aryl group having 6 to 12 C atoms --.

Signed and Sealed this  
Fourteenth Day of December, 2021

Drew Hirshfeld  
*Performing the Functions and Duties of the*  
*Under Secretary of Commerce for Intellectual Property and*  
*Director of the United States Patent and Trademark Office*